United States Patent [19]

Bitter

[11] Patent Number: 4,977,092
[45] Date of Patent: Dec. 11, 1990

[54] EXPRESSION OF EXOGENOUS POLYPEPTIDES AND POLYPEPTIDE PRODUCTS INCLUDING HEPATITIS B SURFACE ANTIGEN IN YEAST CELLS

[75] Inventor: Grant A. Bitter, Thousand Oaks, Calif.

[73] Assignee: Amgen, Thousand Oaks, Calif.

[21] Appl. No.: 231,599

[22] Filed: Aug. 8, 1988

Related U.S. Application Data

[63] Continuation of Ser. No. 748,712, Jun. 26, 1985, abandoned, which is a continuation of Ser. No. 412,707, Aug. 30, 1982, abandoned.

[51] Int. Cl.$^5$ .................. C12N 15/00; C12N 1/16; C12N 1/18; C12P 21/00
[52] U.S. Cl. ................... 435/320; 435/69.3; 435/71.1; 435/172.3; 435/255; 435/256; 935/34; 935/37; 935/69
[58] Field of Search ............ 435/68, 70, 71, 91, 435/172.1, 172.3, 255, 256, 320, 69.1, 69.3, 69.9, 71.1; 536/27; 935/34, 37, 69

[56] References Cited

U.S. PATENT DOCUMENTS

| | | | |
|---|---|---|---|
| 4,446,235 | 5/1984 | Seeburg | 435/91 |
| 4,599,311 | 7/1986 | Kawasaki | 435/71 |
| 4,615,974 | 10/1986 | Kingsman et al. | 435/68 |
| 4,769,238 | 9/1988 | Rutter et al. | 435/70 |
| 4,803,164 | 2/1989 | Hitzeman et al. | 435/68 |

OTHER PUBLICATIONS

Valenzuela et al., "Nucleotide sequence of the gene coding for the major protein of hepatitis B virus surface antigen", Nature 280:815 (1979).
Botstein et al., "Sterile host yeasts(SHY): A eukaryotic System of biological containment for recombinant DNA experiments", Recombinant DNA Technical Bulletin 2 (2): 49 (1979).
Holland et al., "Isolation and characterization of a gene coding for glyceraldehyde-3-phosphate dehydrogenase from Saccharomyces cerevisiae", J. Biol. Chem. 254: 5466 (1979).
Holland et al., "The primary structure of a glyceraldehyde-3-phosphate dehydrogenase gene from Saccharomyces cerevisiae", J. Biol. Chem. 254: 9839 (1979).
Holland et al., "Structural comparison of two nontandemly repeated yeast glyceraldeyde-3-phosphate dehydrogenase genes", J. Biol. Chem. 255: 2596 (1980).
Ammerer et al.: in Recombinant DNA, Walton (ed.), Elsevier Scientific Publishing Co., New York, 1981, pp. 185–197.
Grantham et al., "Codon frequencies in 119 individual genes confirm consistent choices of degenerate bases according to genome type", Nucleic Acids. Research 8(9), 1893 (1980).
Beggs, Nature, 275: 104–109 (1979).
Bennetzen et al., J. Biol. Chem., 257: 3018–3025 3026–3031 (1982).
Dreesman et al., Nature, 295: 158–160 (1982).
Edman et al., Nature, 291: 503–506 (1981).
Grantham et al., Nucleic Acids Research, 8: r49–r62 (1980).
Grantham et al., Nucleic Acids Research, 9: r43–r74 (1981).
Hall et al., DNA, 2: 182 (1982).
(List continued on next page.)

Primary Examiner—James Martinell
Attorney, Agent, or Firm—Marshall, O'Toole, Gerstein, Murray & Bicknell

[57] ABSTRACT

Novel yeast cell transformation vectors are manufactured and employed in securing expression of exogenous polypeptides in yeast cells. Vectors include promoter/regulator DNA sequences of yeast glyceraldehyde-3-phosphate dehydrogenase gene origins. In an illustrative preferred embodiment, novel immunologically active hepatitis B surface antigen (HBsAg) preparations are isolated from yeast cells transformed with plasmid A.T.C.C. 40053. These HBsAg preparations of yeast origin may be incorporated into vaccine compositions useful in developing immunological responses protective against infection by hepatitis B virus.

10 Claims, 2 Drawing Sheets

OTHER PUBLICATIONS

Hinnen et al., *Proc. Natl. Acad. Sci. USA*, 75: 1929–1933 (1978).

Hitzeman et al., *J. Biol. Chem.*, 255: 12073–12080 (1980).

Hitzeman et al., *Nature*, 293: 717–722 (1982).

Hsiao et al., *Proc. Natl. Acad. Sci. USA*, 76: 3829–3833 (1979).

Kingsman et al., *Gene*, 7: 141–153 (1979).

Stinchcomb et al., *Nature*, 282: 39–43 (1979).

Stinchcomb et al., *Proc. Natl. Acad. Sci. USA*, 77: 4559 (1980).

Struhl et al., *Proc. Natl. Acad. Sci. USA*, 76: 1035–1039 (1979).

Valenzuela et al., *Nature*, 298: 347–350 (Jul. 1982).

Zaret et al., *Cell*, 28: 563–573 (1982).

"BRL Restriction Endonuclease Reference Chart" in the '81/'82 Catalog of Bethesda Research Laboratories, Inc., Gaithersburg, MD.

Musti et al., *Gene*, 25: 133–143 (1983).

Holland et al., *J. Biol. Chem.*, 258(8): 5291–5299 (Apr. 1983).

1

EXPRESSION OF EXOGENOUS POLYPEPTIDES AND POLYPEPTIDE PRODUCTS INCLUDING HEPATITIS B SURFACE ANTIGEN IN YEAST CELLS

This application is a continuation of application Ser. No. 748,712 filed June 26, 1985, now abandoned, which is a continuation of application of Ser. No. 412,707 filed Aug. 30, 1982, now abandoned.

BACKGROUND

The present invention relates, in part, to manipulation of genetic materials including the manufacture of specific DNA sequences useful in recombinant procedures to secure the production of proteins of interest by microorganisms. The present invention also relates to novel immunologically active substances produced by recombinant methodologies and, more particularly to novel preparations of hepatitis B surface antigen (HBsAg) of yeast cell origin.

A. Manipulation Of Genetic Materials

Genetic materials may be broadly defined as those chemical substances which program for and guide the manufacture of constituents of cells and viruses and direct the responses of cells and viruses. A long chain polymeric substance known as deoxyribonucleic acid (DNA) comprises the genetic material of all living cells and viruses except for certain viruses which are programmed by ribonucleic acids (RNA). The repeating units in DNA polymers are four different nucleotides, each of which consists of either a purine (adenine or guanine) or a pyrimidine (thymine or cytosine) bound to a deoxyribose sugar to which a phosphate group is attached. Attachment of nucleotides in linear polymeric form is by means of fusion of the 5' phosphate of one nucleotide to the 3' hydroxyl group of another. Functional DNA occurs in the form of stable double stranded associations of single strands of nucleotides (known as deoxyoligonucleotides), which associations occur by means of hydrogen bonding between purine and pyrimidine bases [i.e., "complementary" associations existing either between adenine (A) and thymine (T) or guanine (G) and cytosine (C)]. By convention, nucleotides are referred to by the names of their constituent purine or pyrimidine bases, and the complementary associations of nucleotides in double stranded DNA (i.e., A-T and G-C) are referred to as "base pairs". Ribonucleic acid is a polynucleotide comprising adenine, guanine, cytosine and uracil (U), rather than thymine, bound to ribose and a phosphate group.

Most briefly put, the programming function of DNA is generally effected through a process wherein specific DNA nucleotide sequences (genes) are "transcribed" into relatively unstable messenger RNA (mRNA) polymers. The mRNA, in turn, serves as a template for the formation of structural, regulatory and catalytic proteins from amino acids. This mRNA "translation" process involves the operations of small RNA strands (t+RNA) which transport and align individual amino acids along the mRNA strand to allow for formation of polypeptides in proper amino acid sequences. The mRNA "message", derived from DNA and providing the basis for the tRNA supply and orientation of any given one of the twenty amino acids for polypeptide "expression", is in the form of triplet "codons"—sequential groupings of three nucleotide bases. In one sense, the formation of a protein is the ultimate form of "expression" of the programmed genetic message provided by the nucleotide sequence of a gene.

Certain DNA sequences which usually "precede" a gene in a DNA polymer provide a site for initiation of the transcription into mRNA. These are referred to as "promoter" sequences. Other DNA sequences also usually "upstream" of (i.e., preceding) a gene in a given DNA polymer, bind proteins that determine the frequency (or rate) of transcription initiation. These other sequences are referred to as "regulator" sequences. Thus, sequences which precede a selected gene (or series of genes) in a functional DNA polymer and which operate to determine whether the transcription (and eventual expression) of a gene will take place are collectively referred to as "promoter/regulator" or "control" DNA sequences. DNA sequences which "follow" a gene in a DNA polymer and provide a signal for termination of the transcription into mRNA are referred to as transcription "terminator" sequences.

A focus of microbiological processing for nearly the last decade has been the attempt to manufacture industrially and pharmaceutically significant substances using organisms which do not initially have genetically coded information concerning the desired product included in their DNA. Simply put, a gene that specifies the structure of a product is either isolated from a "donor" organism or chemically synthesized and then stably introduced into another organism which is preferably a self-replicating unicellular microorganism. Once this is done, the existing machinery for gene expression in the "transformed" host cells operates to construct the desired product.

The art is rich in patent and literature publications relating to "recombinant DNA" methodologies for the isolation, synthesis, purification and amplification of genetic materials for use in the transformation of selected host organisms. U.S. Letters Patent No. 4,237,224 to Cohen, et al., for example, relates to transformation of procaryotic unicellular host organisms with "hybrid" viral or circular plasmid DNA which includes selected exogenous DNA sequences. The procedures of the Cohen, et al. patent first involve manufacture of a transformation vector by enzymatically cleaving viral or circular plasmid DNA to form linear DNA strands. Selected foreign ("exogenous" or heterologous") DNA strands are also prepared in linear form through use of similar enzymes. The linear viral or plasmid DNA is incubated with the foreign DNA in the presence of ligating enzymes capable of effecting a restoration process and "hybrid" vectors are formed which include the selected foreign DNA segment "spliced" into the viral or circular DNA plasmid.

Transformation of compatible unicellular host organisms with the hybrid vector results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of commercially significant protein or polypeptide fragments coded for by the foreign DNA. See also, e.g., U.S. Pat. Nos. 4,264,731 (to Shine), 4,273,875 (to Manis) and 4,293,652 (to Cohen).

The success of procedures such as described in the Cohen, et al. patent is due in large part to the ready availability of "restriction endonuclease" enyzmes which facilitate the site-specific cleavage of both the unhybridized DNA vector and, e.g., eucaryotic DNA strands containing the foreign sequences of interest. Cleavage in a manner providing for the formation of single stranded complementary "ends" on the double stranded linear DNA strands greatly enhances the likelihood of functional incorporation of the foreign DNA into the vector upon "ligating" enzyme treatment. A large number of such restriction endonuclease enzymes are currently commercially available [See, e.g., "BRL Restriction Endonuclease Reference Chart" appearing in the "'81/'82 Catalog" of Bethesda Research Laboratories, Inc., Gaithersburg, Maryland.] Verification of hybrid formation is facilitated by chromatographic techniques which can, for example, distinguish the hybrid plasmids from non-hybrids on the basis of molecular weight. Other useful verification techniques involve radioactive DNA hybridization.

Another manipulative "tool" largely responsible for successes in transformation of procaryotic cells is the use of selectable "marker" gene sequences. Briefly put, hybrid vectors are employed which contain, in addition to the desired foreign DNA, one or more DNA sequences which code for expression of a phenotypic trait capable of distinguishing transformed from non-transformed host cells. Typical marker gene sequences are those which allow a transformed procaryotic cell to survive and propagate in a culture medium containing metals, antibiotics, and like components which would kill or severely inhibit propagation of non-transformed host cells.

Successful expression of an exogenous gene in a transformed host microorganism depends to a great extent on incorporation of the gene into a transformation vector with a suitable promoter/regulator region present to insure transcription of the gene into mRNA and other signals which insure translation of the mRNA message into protein (e.g., ribosome binding sites). It is not often the case that the "original" promoter/regulator region of a gene will allow for high levels of expression in the new host. Consequently, the gene to be inserted must either be fitted with a new, host-accommodated transcription and translation regulating DNA sequence prior to insertion or it must be inserted at a site where it will come under the control of existing transcription and translation signals in the vector DNA.

Expression of Genes By Yeast Cells

Of particular interest to the background of the present invention of novel transformation vectors are those publications which provide information concerning the general nature of expression of polypeptides in yeast cells (e.g., *Saccharomyces cerevisiae*) as well as those which describe attempts to employ yeast cells as host cells for the expression of exogenous (e.g., mammalian) genes which code for commercially useful polypeptides. Yeast cells comprise particularly interesting potential host cells for practice of recombinant method directed toward expression of glycoproteins because the existing synthetic apparatus of these cells has the capacity to generate glycosylated proteins.

Illustrative of those publications focusing on the general nature of gene expression in yeast cells are those reporting on studies of the primary structure of genes coding for synthesis of endogenous yeast enzymes. See, e.g., Holland and Holland, *J. Biol. Chem.*, 254, pp. 9839-9845 (1979) discussing the yeast glyceraldehyde-3-phosphate dehydrogenase (G-3-PDH) gene; Hitzeman, et al., *J. Biol. Chem.*, 255, pp. 12073-12080 (1980) discussing the yeast 3-phosphoglycero kinase (PGK) gene; and, Bennetzen and Hall, *J. Biol. Chem.*, 257, pp. 3018-3025 (1982) discussing the yeast alcohol dehydrogenase I (ADHI) gene. Publications treating genes coding for polypeptides whose presence or absence can serve as metabolic markers for potential yeast cell transformation vectors include: Hinnen, et al., *Proc. Natl. Acad. Sci. U.S.A.*, 75, pp. 1929-1933 (1978) discussing the yeast LEU2 gene coding for the leucine biosynthetic enzyme, β-isopropyl-malate dehydrogenase; and Tschumper and Carbon, *Gene*, 16, pp. 157-166 (1980) which discusses the yeast TRP1 gene which codes for the tryptophane biosynthetic enzyme phosphoribosyl anthranilate isomerase.

A number of prior publications treat autonomous replicating DNA sequences, "ARS's", which confer the capacity for autonomous replication of contiguous DNA sequences and are thus significantly involved in insuring autonomous replication of DNA transformation vectors in yeast cells. Beggs, *Nature*, 275, pp. 104-109 (1979) discusses the so-called "2μ" origin of replication". See, also, Stinchcomb, et al., *Proc. Natl. Acad. Sci. U.S.A.*, 77, pp. 4559 (1980) which treats DNA sequences of non-yeast origins which are capable of functioning as ARS's in yeast. Struhl, et al., *Proc. Natl. Acad. Sci. U.S.A.*, 76, pp. 1035-1039 (1979) discusses the so-called "ARS 1" origin of replication sequence obtained as a 1453 base pair fragment of yeast DNA upon digestion with the restriction endonuclease enzyme, EcoRI. Hsiao and Carbon, *Proc. Natl. Acad. Sci. U.S.A.*, 76, pp. 3829-3833 reports the isolation of an ARS on a fragment containing the yeast ARG 4 gene.

The above-noted Struhl, et al. reference is of interest for its discussion of the ARS 1 origin of replication in the context of the development of a particular kind of yeast transformation vector, yeast-bacterial hybrid plasmids. These plasmids are able to replicate in (and may be selected in and recovered from) both *E. coli* (wherein it is preferred to effect vector construction and amplification) and *Saccharomyces cerevisiae* (wherein it may be desired to secure DNA expression). The development and properties of such hybrid plasmids, commonly referred to as "shuttle vectors" has subsequently been extensively treated in Stinchcomb, et al., *Nature*, 282, pp. 39-43 (1979); Kingsman, et al., *Gene*, 7, pp. 141-153 (1979); and, Tschumper and Carbon, *Gene*, 10, pp. 157-166 (1980). These references specifically discuss the yeast bacterial plasmid designated YRp7.

Finally, the efficiency of termination of transcription of eucaryotic genes, including yeast genes, into mRNA has been the subject of many recent studies. A summary of the more significant findings of such studies may be found in Zaret, et al., *Cell*, 28, pp. 563-573 (1982), which itself treats transcription efficiency for mutant and wild type yeast CYC1 genes. Briefly put, efficient transcription of yeast DNA into mRNA appears to be significantly dependent upon the presence or absence of either a site for so-called "poly-A addition" (typically an AATAAA sequence), or a "transcription termination" sequence, or both such sequences, at or near the 3' end of a polypeptide coding region of a gene.

While the above-noted references have provided a great deal of information which is relevant to the goal of securing expression of exogenous genes in yeast cells, reports of successful, stable yeast cell transformations with accompanying high levels of expression of exogenous genes are exceedingly few. For example, very recent publications have dealt with successful attempts to secure expression of human leucocyte interferon D [Hitzeman, et al., *Nature*, 293, pp. 717–722 (1982)] and unsuccessful attempts to secure expression of rat growth hormone [Ammerer, et al., *Recombinant DNA, Proc. 3rd Cleveland Symp. Macromolecules* (ed. Walton, AG), pp. 185–197, (Elsevier Amsterdam, 1981)]. In each instance, the work involved construction of yeast expression vectors which combine a selectable marker (LEU2 or TRP1), a yeast replication origin (ARS1 or the 2µ origin) as well as what are generically referred to as "transcription initiation and termination-specifying sequences, primarily from the yeast ADH1 gene". In each instance an intron-free gene of mammalian origin was inserted 3' to an ADH1 promoter/regulator region fragment and 5' to a yeast TRP1 gene, viz, 5'-ADH1 promoter-3', 5'-mammalian gene-3',5'-TRP1-3'.

The "mixed" results of this research involving essentially identical procedures practiced by the same group of researchers but generating significantly different results in terms of protein expression were recently summarized in an abstract by Hall and Ammerer appearing in *DNA*, 2, page 182 (1982) wherein it was noted, "By joining the 5' flanking sequences of the yeast ADH1 structural gene to the coding sequences of other genes (yeast CYC1, rat growth hormone cDNA, human LeIF$_D$, hepatitis B surface antigen) ADH1 transcription starting specificity is transplanted and expression is promoted. While the requirements for transcription initiation are easily met, expression at the protein level is not observed in all cases". Differences in results were generally attributed to variations in "posttranscriptional events" of various possible types.

There thus continues to be a need in the art for yeast cell transformation vectors useful in securing the high level expression in yeast host cells of exogenous genes coding for useful proteins.

C. Hepatitis B Surface Antigen

Of particular interest to the background of the novel preparations of the present inventions which display the immunological activity of hepatitis B surface antigen are the numerous publications and patents treating the nature of the hepatitis B viral disease state as well as methods and materials developed for preparing vaccines protective of susceptible mammals against viral infection.

Hepatitis B virus constitutes a public health problem of enormous proportions affecting some 2 million persons worldwide. In the U.S. alone, some 100,000 to 200,000 cases of hepatitis are annually attributed to infection by this virus and it is reliably estimated that such infection results in nearly 2,000 fatalities each year. A major step in the prophylaxis against hepatitis B infection was the 1965 discovery of various circulating antigen particles in the serum of infected mammals, including humans. In the early 1970's, it was established that subunit vaccines comprising hepatitis B surface antigen preparations isolated from the plasma of chronic carriers could provide a protective immune response against infection by the virus. Since that time, enormous research and developmental effort has been expended with the goal of optimizing the procedures by which the surface antigen (HBsAg) could be isolated in quantity and incorporated into effective vaccine compositions. Reflecting this effort are the numerous U.S. Letters Patent in this subject area which have issued in the last five years alone, including U.S. Pat. Nos. 4,024,243; 4,057,628; 4,113,712; 4,017,360; 4,118,477; 4,118,478; 4,129,646; 4,138,287; 4,186,193; 4,164,565; and U.S. Pat. No. 4,242,324.

A hepatitis B vaccine composition very recently made available is the product marketed by Merck, Sharp and Dohme, Inc. as "Heptavax-B". This product is recommended for immunization against infection caused by all known subtypes of hepatitis B virus in persons 3 months of age or older. Each 1.0 ml dose of the vaccine contains 20 µg of hepatitis B surface antigen formulated in an alum adjuvant. The immunization regimen consists of 3 doses of vaccine given intramuscularly, with dose volumes ranging from 0.5 to 2.0 ml according to the age, weight or other characteristics of the vaccinate.

The specific antigen preparation employed in the above-noted vaccine consists of purified, antigenic spherical particles of an average dimension of about 22 nanometers (nm) which are isolated from the plasma of chronic carriers by such exhaustive purification methods as fractional precipitation, chromatographic separation, sequential isopycnic and rate zonal centrifugation, peptic digestion and various chemical treatments.

Upon isolation from plasma, the active, HBsAg subunit vaccine particle preparations are characterized by a lipoproteinaceous constitution wherein the major phospholipids are identified as phosphotidylcholine and sphingomyelin. There has also been found evidence of carbohydrate in HBsAg preparations in the form of glycoproteins and/or glycolipids. Degradative analysis of the protein moiety of the HBsAg preparations purified from plasma has revealed mixtures of polypeptides ranging in molecular weight from 19,000 to 120,000 daltons.

As a result of the above-noted physical characteristics, the 22 nm HBsAg particle is frequently visualized as comprising disulfide-bonded pairs of identical polypeptide strands (each of about 25,000 daltons) having lipids associated with and shrouding hydrophobic amino acid rich regions and also possibly having carbohydrates linked to exposed hydrophilic amino acid-rich regions which generally "present" short, antigenic polypeptide sequences to the host.

The HBsAg in the lipid envelope has one well-characterized group specific determinant, a, and two sets of mutually exclusive subtype determinants, d/y and w/r. Four major subtypes of HBsAg exist: adw, ayr, ayw, and adr. Other intermediate specificities have led to the classification of HBsAg into ten serological categories.

Numerous attempts have been made to dispositively ascertain the amino acid sequence of the major protein(s) of HBsAg and the nucleotide sequence of the viral gene coding for the protein. For example, Valenzuela, et al. *Nature*, 280, pp. 815–819 (1979) treats the extraction of DNA from hepatitis B viral particles and the cloning and isolation of an 892 base pair fragment believed to encode for the proposed major protein component of HBsAg. Based on nucleotide base sequence analysis, a 226 amino acid polypeptide sequence was deduced which precisely corresponds in its initial N-terminal region to published amino acid sequences for that region ascertained by peptide degradative analysis. The published amino acid sequence is as follows:

| 1 | | | | 5 | | | | 10 | | | | 15 |
|---|---|---|---|---|---|---|---|---|---|---|---|---|
| Met | Glu | Asn | Ile | Thr | Ser | Gly | Phe | Leu | Gly | Pro | Leu | Val | Leu |

-continued

```
             20                  25                 30
Gln Ala Gly Phe Phe Leu Leu Thr Arg Ile Leu Thr Ile Pro Gln 35                  40                 45
Ser Leu Asp Ser Trp Trp Thr Ser Leu Asn Phe Leu Gly Gly Ser 50                  55                 60
Pro Val Cys Leu Gly Gln Asn Ser Gln Ser Pro Thr Ser Asn His 65                  70                 75
Ser Pro Thr Ser Cys Pro Pro Ile Cys Pro Gly Tyr Arg Trp Met 80                  85                 90
Cys Leu Arg Arg Phe Ile Ile Phe Leu Phe Ile Leu Leu Leu Cys 95                 100                105
Leu Ile Phe Leu Leu Val Leu Leu Asp Tyr Gln Gly Met Leu Pro 110                 115                120
Val Cys Pro Leu Ile Pro Gly Ser Thr Thr Thr Ser Thr Gly Pro 125                 130                135
Cys Lys Thr Cys Thr Thr Pro Ala Gln Gly Asn Ser Met Phe Pro 140                 145                150
Ser Cys Cys Cys Thr Lys Pro Thr His Gly Asn Cys Thr Cys Ile 155                 160                165
Pro Ile Pro Ser Ser Trp Ala Phe Ala Lys Tyr Leu Trp Glu Trp 170                 175                180
Ala Ser Val Arg Phe Ser Trp Leu Ser Leu Leu Val Pro Phe Val 185                 190                195
Gln Trp Phe Val Gly Leu Ser Pro Thr Val Trp Leu Ser Ala Ile 200                 205                210
Trp Met Met Trp Tyr Trp Gly Pro Ser Leu Tyr Ser Ile Val Ser 215                 220                225
Pro Phe Ile Pro Leu Leu Pro Ile Phe Phe Cys Leu Trp Val Tyr

Ile.
```

The above-noted work directed toward amino acid analysis of polypeptide constituents of HBsAg preparations has been of significant value to those seeking to develop synthetic vaccines, i.e., "second generation" hepatitis B polypeptide vaccines containing hepatitis B-specific antigenic components. See, e.g., Dreesman, et al., *Nature*, 295, pp. 158–160 (1982), Edman, et al., *Nature,* 291, pp. 503–506 (1981) and Zuckerman, *Nature,* 295, pp. 98–99 (1982). In the Dreesman, et al. publication, it was reported that synthetic peptide sequences of 16 to 21 amino acids duplicative of putative HBsAg sequences appeared to be capable of stimulating antibody production responses in host animals even without "mounting" of the sequences on carrier particles. No immunoprotective properties were attributed to the sequences, however. In the Edman, et al. publication, work on bacterial synthesis of HBsAg sequences as fusion polypeptides is reported. These polypeptides appeared to include one or more antigenic determinations found in native HBsAg and, while investigation into immunogenic characteristics was projected, immunoprotective properties on par with carrier-derived 22 nm particles was not expected to be obtained. In the Zuckerman publication, it was reported that, "Expression of glycosylated hepatitis B surface antigen in yeast cells has recently been reported by W. J. Rutter of the University of California, San Francisco, and this is potentially a most important development for large-scale in vitro production of an immunogen". The text, however, provides no particulars as to the physical nature of the glycoprotein antigen, its immunological characteristics, or the manner and quantities in which it may have been obtained.

Only very recently has any detailed report been published concerning the work on HBsAg announced by Zuckerman, supra. Specifically, an article by Valenzuela, et al. appearing in *Nature,* 298, pp. 347–350 (July 22, 1982) reports on the synthesis and assembly of Hepatitis B virus surface antigen particles in yeast. Briefly summarized, the HBsAg antigen was noted to have been synthesized in yeast using an expression vector that employed the 5′ flanking region of yeast alcohol dehydrogenase I as a promoter to transcribe surface antigen coding sequences. The protein synthesized in yeast was said to have been assembled into particles having properties similar to the 22 nm particles secreted by human cells. The publication of Valenzuela, et al., *Nature,* 298, pp. 347–350 (1982) is specifically incorporated herein for purposes of providing information relevant to the background of the present invention.

While significant advances appear to have been made toward the procurement of immunologically active HBsAg preparations from sources other than human carrier plasma, prior to the present invention the art had not been provided with certain means for obtaining such preparations in significant quantity, nor had the fragmentary reports of successes in this area been accompanied by any showing of useful immunoprotective properties.

BRIEF SUMMARY

In one of its aspects, the present invention provides a new class of transformation vectors which facilitate the high level expression in yeast cells of genes which are exogenous to yeast and which code for commercially useful polypeptides. More specifically provided are yeast cell transformation vectors comprising: (1) a DNA transcription promoter/regulator DNA sequence endogenous to yeast cell synthesis of mRNA coding for glyceraldehyde-3-phosphate dehydrogenase; (2) a DNA sequence transcribable into mRNA coding for synthesis of a polypeptide exogenous to yeast cells; (3) a DNA sequence coding for termination of transcription of and/or poly-A addition to mRNA in yeast cells; and (4) a DNA sequence operative in yeast cells to confer to said vector the capacity for autonomous DNA replication. The vectors may also desirably contain DNA sequences which allow selection of yeast cells containing the vectors.

In preferred embodiments of vectors constructed according to the invention, the promoter/regulator region substantially duplicates portions of the putative promoter/regulator region of a glyceraldehdge-3-phosphate dehydrogenase (G-3-PDH) gene of yeast cell line *Saccharomyces cerevisiae* S288C. This DNA fragment can be isolated as an approximately 680 base pair fragment by TaqI restriction endonuclease enzyme digestion of a cloned 2.1 kilobase Hind III fragment containing the G-3-PDH gene. Preferred embodiments of vectors also include, e.g., a 2$\mu$ replicon or autonomous replicating sequences such as ARS-1 and may also have mRNA transcription termination and/or poly-A addition sequences provided as a portion of a TRPl gene located 3′ and in the same polarity to the exogenous gene whose expression is sought. When an entire TRPl gene is employed to supply transcription termination and/or poly-A addition sequences, it may serve as a selectable marker for yeast transformation and vector maintenance. The 3′ ends of other yeast genes which include sequences responsible for transcription termination and/or poly-A addition may also be utilized.

Because the manufacture of yeast transformation vector of the invention ordinarily involves carrying out manipulations of DNA sequences in bacterial cells, the vectors may retain some or all of the requisite properties of "shuttle" vectors, i.e., DNA sequences providing for autonomous replication and selectable transformation in bacteria.

Also comprehended by the invention are transformation procedures for securing the expression, in yeast cells, of exogenous polypeptide sequences and for forming novel isolatable proteinaceous products including not only polypeptides (proteins) but also lipoproteins, glycoproteins and glycolipoproteins. Such products are unique in terms of their in vitro origins in yeast cells (rather than the life forms to which they are endogenous) and may also be uniquely characterized by the presence of carbohydrate and/or lipid constituents peculiar to their yeast cell origins.

DNA sequences transcribable into mRNA for exogenous polypeptides may derive from a wide variety of life forms including procaryotic and eucaryotic cells and viruses. The most commercially significant DNA sequences for incorporation into vectors of the invention are of eucaryotic origin and, consistent with prior studies of yeast expression, preferably are free of introns. DNA sequences may be cloned genomic isolates, cDNA's or totally or partially manufactured DNA sequences.

Illustrative of an exogenous DNA sequence constituent of vectors of the invention is a DNA sequence transcribable into mRNA coding for synthesis, in yeast, of a polypeptide having one or more of the immunological activities of HBsAg. Also illustrated are DNA sequences which comprise a series of base codons duplicative of codons endogenous to the HBsAg gene in hepatitis B viral genome and a manufactured sequence of base codons selected on the basis of optimal yeast codon preferences.

In another of its aspects, the present invention provides novel preparations possessing one or more of the immunological activities of HBsAg, which preparations may suitably be employed in the manufacture of vaccine compositions. The vaccine compositions so manufactured may be employed in the manner of commercial HBsAg vaccines to provoke the formation of antibodies protective against hepatitis B virus infection of a susceptible mammalian species vaccinate. Additionally, HBsAg preparations of the invention are expected to be quite usefully employed as reagents in procedures for quantitative detection of hepatitis B virus associated markers in fluid samples.

The novel HBsAg preparations of the present invention include proteinaceous materials isolated from genetically transformed yeast cells, which materials (a) respond positively in standardized radioimmunoassays or enzyme linked immunoassays for HBsAg of serum origin; (b) are immunologically neutralized by human antibodies to HBsAg; (c) sediment at greater than 28 S in sucrose gradients; and (d) have a buoyant density in cesium chloride which is somewhat less than that of HBsAg particles of virally-infected human serum origin (i.e., less than 1.210). These proteinaceous yeast cell products are thus believed to be lipoproteins which may also be glycosylated and appear to have a spherical particulate configuration.

A DNA vector, pHBs-1[GPD] suitable for use in practice of the invention to stably transform yeast cells and to thereby secure the expression of readily isolatable quantities of a lipoprotein preparation having one or more of the immunological activities of HBsAg of viral origin was deposited with the American Type Culture Collection, 12301 Parklawn Drive, Rockville, Maryland, 20852 on Aug. 20, 1982, in accordance with the Patent and Trademark Office's requirements for microorganism deposits, and was designated as A.T.C.C. No. 40053.

Further aspects and advantages of the present invention will be apparent upon considerations of the following detailed description of the practice of preferred embodiments thereof, reference being made to FIGS. 1 through 4 which provide schematic illustrations of certain genetic manipulations performed according to the invention and certain DNA sequences involved in these manipulations.

DETAILED DESCRIPTION

Figure 1:
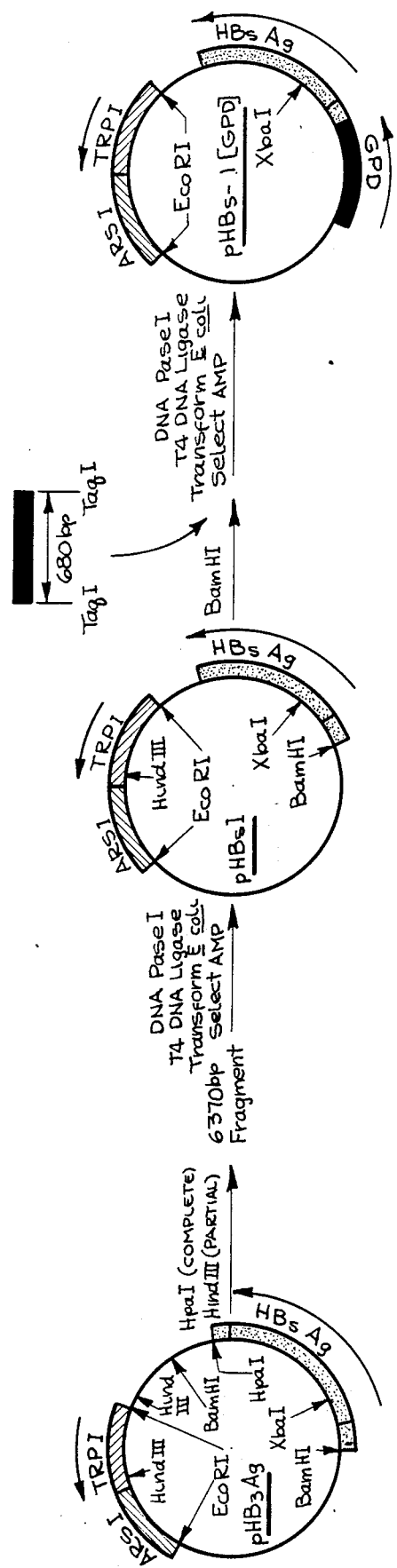
FIG. 1 shows the construction of pHBs-1[GPD[.

The following examples illustrate practice of the invention in the construction of illustrative yeast cell transformation vectors, including pHBs-1[GPD] [A.T.C.C. No. 40053] and in the preparation and characterization of novel lipoprotein products of yeast origin which possess immunological activities ordinarily displayed by HBsAg of viral origin. More particularly, Examples 1 through 4 are directed to the following manipulations performed with respect to plasmid pHBsAg comprising the shuttle vector, YRp7 (pRB16, A.T.C.C. 37052), into which had been cloned a 1350 base pair genomic DNA fragment of hepatitis B origin including a HBsAg gene; deletion from pHBsAg of HBV DNA sequences 3' to the HBsAg coding region; isolation of a putative promoter/regulator DNA sequence fragment from a G-3-PDH gene of yeast cell line Saccharomyces cerevisiae S288C; insertion of the promoter/regulator DNA sequence 5' to the HBsAg gene in pHBsAg to form plasmid pHBs-1[GPD]; and transformation of yeast cells with the pHBs-1[GPD]. Examples 5 through 9 relate to characterization of novel lipoprotein HBsAg products of yeast origin in term of their physical properties and immunological activities. Also provided are constructions of additional transformation vectors which include DNA sequences coding for HBsAg synthesis in yeast.

DNA sequences according to the present invention may also be manufactured using one or more of the "optimal" yeast preference codons set forth in Table I. [See Bennetzen, et. al., *J. Biol. Chem.*, 257, 3026–3031, (1982)]

TABLE I

| Amino Acid | "Optimal" Codon |
|---|---|
| Ala | 5'-GCT or 5'-GCC |
|  | CGA CGG |
| Arg | 5'-AGA |
|  | TCT |
| Asp | 5'-GAC |
|  | CTG |
| Asn | 5'-AAC |

TABLE I-continued

| Amino Acid | "Optimal" Codon |
|---|---|
| | TTG |
| Cys | 5'-TGT |
| | ACA |
| Gln | 5'-CAA |
| | GTT |
| Glu | 5'-GAA |
| | CTT |
| Gly | 5'-GGT |
| | CCA |
| His | 5'-CAC |
| | GTG |
| Ile | 5'-ATT or 5'-ATC |
| | TAA TAG |
| Leu | 5'-TTG |
| | AAC |
| Lys | 5'-AAG |
| | TTC |
| Phe | 5'-TTC |
| | AAG |
| Pro | 5'-CCA |
| | GGT |
| Thr | 5'-ACT or 5'-ACC |
| | TGA TGG |
| Tyr | 5'-TAC |
| | ATG |
| Ser | 5'-TCT or 5'-TCC |
| | AGA AGG |
| Val | 5'-GTT or 5'-GTC |
| | CAA CAG |

EXAMPLE 1

A DNA plasmid designated pHBsAg was obtained from collaborators at Abbott Laboratories, North Chicago, Illinois. The plasmid was reported to have been constructed by manipulations performed on a yeast-bacteria shuttle vector, YRp7 (A.T.C.C. 37052). More specifically, in a manner analogous to that illustrated for preparation of the bacterial plasmid pHBV-3200 from pBR322 by Valenzuela, et al., supra, a 1350 base pair DNA fragment obtained by BamHI treatment of a cloned hepatitis B genome was inserted at the BamHI site of YRp7 using T4 DNA ligase. The fragment was inserted in the same polarity as the TRP1 gene of YRp7 at the BamHI site about 400 base pairs 5' to the TRP1 gene. The resultant vector was amplified by transformation of E. coli accompanied by selection based on the presence of the AMP gene marker native to YRp7.

Upon receipt of the plasmid, partial DNA sequence analysis and restriction enzyme mapping of the inserted fragment was conducted and revealed (reading 5' to 3'): (1) the 5' end BamHI cleavage site occurs 126 base pairs 5' to the first ATG codon (transcribable to an AUG mRNA translation initiation codon) in the sequence; (2) an XbaI recognition site mapped by restriction enzyme digestion exists in the polypeptide coding region commencing about 94 base pairs 3' to the above-noted ATG codon and about 218 base pairs 3' to the BamHI cleavage site; (3) a unique HpaI recognition site mapped by restriction enzyme digestion exists approximately 715 base pairs 3' to the XbaI recognition site and 933 base pairs 3' to the BamHI cleavage site; and (4) the 3' BamHI cleavage site is approximately 440 base pairs 3' to the HpaI cleavage site. Observed characteristics (1) and (2), above, are in accord with the DNA sequence published by Valenzuela, et al., supra. Specific sequencing of the top strand (5' to 3') revealed the following as the identities of the first 143 bases of the HBV fragment:

```
 BamHI                             *
GGATCCCAGAGTCAGGGGTCTGTATTTTCCTGCTGGTGGCTCCAGTTCAGGAACAGT

AAACCCTGCTCCGAATATTGCCTCTCACATCTCGTCAATCTCCGCGAGGACTGGGGA

CCCTGTGACGAACATGGAGAACATCACATCAGGATTCCTA....
```

Except that a thymine rather than cytosine was identified at the site designated by an asterisk, the sequence is in complete accord with that of Valenzuela, et al., supra. The HBsAg gene insert, which was cloned from pooled sera, is presumably of serotype adw 2 reported by Valenzuela, et al.. It is noteworthy that this fragment includes an adenine base at a position "−3" to the ATG. This is a feature believed to be present in most endogenous yeast structural genes and which has been implicated as significant to gene expression.

EXAMPLE 2

Plasmid pHBsAg was reconstructed by deletion of certain DNA sequences intermediate the HBsAg gene and the TRP1 gene as follows. The plasmid was completely digested with HpaI restriction endonuclease. The linearized product was then partially digested using Hind III resulting in formation of a mixture of linear fragments which differed in length depending on which of the two Hind III recognition sites provided the cleavage site. The approximately 6370 base pair fragment (which retained the Hind III recognition site within the yeast TRP1 gene but was cleaved at the Hind III site of pBR322) was purified. The cohesive ends of the fragment were then filled in (i.e., rendered "blunt") with DNA Polymerase I large fragment (Klenow fragment) (Bethesda Research Labs.) and the plasmid religated using T4 ligase. The resulting circularized DNA plasmid, pHBs-1, was amplified and purified through transformation of E. coli accompanied by selection based on the presence of the AMP gene marker. The net result of the procedure was the elimination of an approximately 780 base pair fragment of both HBV and pBR322 origin, bringing the TRP1 gene into close proximity to, and in the same polarity with, the HBsAg gene. This projectedly facilitates yeast RNA polymerase II transcription of the TRP1 gene by "read-through" transcription from the surface antigen gene. This, in turn, functionally associates such transcription termination and/or poly-A addition sequences as are extant in the yeast TRP1 gene with the HBsAg gene so that transcriptional events attending HBsAg mRNA formation based on vector DNA closely simulate those of endogenous genes. Additionally, plasmid pHBs-1 contains a unique BamHI site 126 bp upstream from the ATG initiator of the surface antigen gene. There are no ATG sequences in the coding strand between the BamHI site and the ATG initiator of the surface gene. Thus, this unique BamHI site may be used for cloning and functional testing of putative yeast promoter fragments.

EXAMPLE 3

A yeast glyceraldehyde-3-phosphate dehydrogenase gene DNA fragment never before shown to be a promoter was isolated for use as a promoter/regulator sequence in vectors of the invention according to the following procedure. A 2.1 kilobase yeast Hind III fragment containing the G-3-PDH gene isolated from a phage lambda yeast DNA library of yeast cell line S288C, was subcloned in pBR322. (Dr. R. A. Kramer, Nat'l. Cancer Inst., Nat'l. Institute of Health, Bethesda, Md., Musti, et al., 1981 Cold Spring Harbor Meeting, Abstract No. 215, Cold Spring Harbor Laboratory; see also, Holland, et al., *J. Biol. Chem.*, 254, pp. 9839–9845 (1979)). This plasmid was digested to completion with Hind III and an approximately 2100 base pair DNA fragment was isolated. This fragment was then digested to completion using TaqI and the largest fragment (approximately 680 base pairs) was purified. Based on prior publications of results of the sequencing of the 5' untranslated region of the yeast G-3-PDH gene, the isolated fragment did not include the 26 base pair sequence

```
CGAATAAACACACATAAATAAACAAA
GCTTATTTGTGTGTATTTATTTGTTT
``` present in the endogenous gene prior to the initial ATG of the structural gene. The DNA fragment used herein as a promoter is the 680 base pair fragment upstream (5' to the coding region) of the 26 base pair sequence noted.

EXAMPLE 4

Plasmid pHBs-1[GPD], A.T.C.C. 40053 was constructed as follows. Copies of plasmid pHBs-1 according to Example 2 were digested to completion with BamHI and mixed with the 680 base pair fragment of Example 3. Cohesive ends were made blunt using DNA Polymerase I large fragment (Bethesda Research Labs), the fragments were ligated with T4 DNA ligase, and *E. coli* clones which contained a single 680 base pair fragment inserted in the correct orientation were isolated. The construction of plasmid pHBs-1[GPD] and its structure are illustrated in pertinent part in FIGS. 1 and 2. The vector is seen to include a putative DNA transcription promoter/regulator DNA sequence endogenous to yeast cell synthesis of mRNA coding for glyceraldehyde-3-phosphate dehydrogenase. This approximately 680 base pair sequence is derived from and substantially duplicates a significant portion of the promoter/regulator region of the G-3-PDH gene of yeast cell line *Saccharomyces cerevisiae* S288C. Following this endogenous yeast sequence is an approximately 126 base pair sequence of viral origin which substantially duplicates the untranslated leader region preceding the initial ATG codon of a HBsAg gene in the hepatitis B viral genome. The vector then includes a DNA sequence transcribable into mRNA coding for the synthesis of a polypeptide exogenous to yeast (i.e., a polypeptide-specifying HBsAg gene) in the same polarity a the promoter/regulator. Approximately 29 base pairs of pBR322 DNA separates the antigen gene from a complete yeast TRP1 gene which includes a base sequence coding for transcription termination of and/or poly-A addition to mRNA in yeast. Finally, the vector includes a DNA sequence (i.e., the ARS-1 sequence) operative in yeast cells to confer upon the vector the capacity for autonomous replication.

EXAMPLE 5

Yeast *Saccharomyces cervisiae* RH218 cells were transformed with the pHBs-1[GPD] vectors of Example 4 according to the procedure of Hinnen, et al., *Proc. Nat'l. Acad. Sci. U.S.A.*, 75, 1929–1933 (1978) with transformants selected on the basis of expression of the TRP1 gene by growth of transformed host cells in minimal media lacking tryptophan. Whole cell protein extracts of transformed cells were prepared by converting transformed yeast cells to spheroplasts with Zymolase 60,000 (Kirin Breweries, Japan) in the presence of the osmotic stabilizer, 0.9 M sorbitol. The spheroplasts were collected by centrifugation and lysed by resuspending in 3 volumes of 25 mM Tris-HCl, pH 7.5. (In some instances, the whole cell lysate was sonicated.) The whole cell lysate was subjected to low-speed centrifugation and the supernatant utilized as the source of yeast-produced HBsAg.

EXAMPLE 6

Whole cell protein extracts of yeast cells transformed according to Example 5 and cultured in the absence of tryptophane were assayed for hepatitis B surface antigen using the Auszyme II Immunoassay kit (Abbott Laboratories, North Chicago, Illinois). Briefly summarized, the procedure provides for quantitative detection of HBsAg in a fluid sample by a "sandwich assay". Beads which are coated with antibody to HBsAg are incubated with a solution which may contain HBsAg. Any HBsAg in the solution will bind to the antibody on the bead. After washing, the beads are incubated with a second solution of antibody to HBsAg. This second antibody is linked to horseradish peroxidase, and will bind to antigen which may have bound to the first antibody on the bead. After washing, the amount of HBsAg bound to the bead is quantitated by assaying the amount of horseradish peroxidase (and hence, second antibody) bound to the bead.

When extracts were prepared from untransformed *Saccharomyces cerevisiae* RH218, no HBsAg reactive material was detected by the above assay. However, when extracts were prepared from the same cells transformed with recombinant plasmid pHBs-1[GPD], HBsAg reactive material was detected. Furthermore, this reactive material exhibits a clear dose response with increasing yeast protein concentration in the Auszyme II reactions.

EXAMPLE 7

To provide confirmation that the immunological activity displayed by whole yeast cell extracts in Example 6 was indeed duplicative of HBsAg of viral origins, tests were conducted to determine whether such activity would be "blocked" or neutralized by pre-incubation with human anti-HBsAg antibody as is characteristic of HBsAg positive human serum samples.

This procedure (Auszyme II Confirmatory Neutralization Test, Abbott Labs.) adds an additional step to the procedure of the Auszyme II assay described in Example 6. Before the addition of the second antibody, the bead is incubated with either negative human serum or human antibody to HBsAg. If a material which gives positive results in the Auszyme II assay is HBsAg, it should react with human antibody to HBsAg and therefore be unable to react with the horseradish peroxidase-linked second antibody. The immunoreaction will have been "neutralized". As a control, HBsAg immunoreactivity should not be effected by an intermediate incubation with negative human serum.

The results of the test procedure are summarized in Table I below and reveal that the Auszyme II reactive material in the preparations of yeast origin is substantially duplicative of the HBsAg antigen in the positive human serum which is commonly employed as a source of ingredients for commercial subunit vaccines.

TABLE II

| SAMPLE | INTERMEDIATE INCUBATION | A492 VALUES |
| --- | --- | --- |
| Negative Human Serum | Negative Human Serum | 0.027 |
| Negative Human Serum | Negative Human Serum | 0.014 |
| Negative Human Serum | Negative Human Serum | 0.012 |
| Positive Human Serum | Negative Human Serum | 2.560 |
| Positive Human Serum | Negative Human Serum | 2.770 |
| Positive Human Serum | Human Anti-HBsAg | 0.053 |
| Positive Human Serum | Human Anti-HBsAg | 0.030 |
| Yeast Extract | Negative Human Serum | 0.808 |
| Yeast Extract | Negative Human Serum | 0.771 |
| Yeast Extract | Human Anti-HBsAg | 0.025 |
| Yeast Extract | Human Anti-HBsAg | 0.028 |

EXAMPLE 8

A gross estimate of the structural size of the yeast-produced HBsAg can be determined by its rate of sedimentation in sucrose gradients.

Yeast whole cell extracts are mixed with Tritium-labelled ribosomal RNA and centrifuged in 5-40% sucrose gradients. Fractions are collected, and sedimentation of the ribosomal RNA is measured by determining radioactivity in individual fractions. Sedimentation of the yeast HBsAg was monitored by assaying fractions with the Auszyme II test (Example 6).

Soluble monomeric protein of the size of HBsAg is expected to sediment at about 2S-3S. The yeast HBsAg sedimented at greater than 28S, indicating aggregation into a larger particle structure.

EXAMPLE 9

The similarities and differences between yeast-produced HBsAg preparations of the invention and HBsAg preparations of human origin as presently employed in commercial vaccines are exemplified by buoyant density characteristics of the two substances in cesium chloride.

Solid cesium chloride is added to the yeast whole cell extract and to positive human serum to give a final density of 1.200 gm/cc to each solution. The solutions are centrifuged to equilibrium and fractions are collected. For each fraction, the density is determined and the amount of HBsAg measured using the Auszyme II test (Example 6).

The buoyant density of the HBsAg in human serum was determined to be approximately 1.210 gm/cc while the yeast origin HBsAg preparations had a buoyant density of 1.196 gm/cc. These results, when considered in light of the previously-noted immunological activity determinations, direct the following conclusions. The yeast-produced HBsAg preparations of the invention possess significant immunological properties which are characteristic of antigen preparations obtained from human carrier serum. The preparations are nonetheless physically distinct substances presumably owing to the presence of yeast origin lipids rather than human origin lipids or some difference in the spectrum of proteins present in the particle.

Purification procedures to be employed to isolate lipid particles containing HBsAg from transformed yeast cells include rate zonal centrifugation, repeated isopycnic centrifugation, fractional precipitation and chromatographic techniques.

Vaccine compositions according to the present invention may be formulated in the same manner as noted above with regard to commercial vaccines incorporating viral origin HBsAg isolates from human serum. Unit doses of 1.0 ml volume may be formulated containing approximately 20μg of antigen isolated from yeast and may include standard immunologically acceptable diluents, adjuvants and carriers. In a like manner, vaccination procedures of the present invention for the purpose of provoking a protective immune response in a susceptible mammal correspond to those practiced using HBsAg vaccine preparations. An exemplary immunization regimen may thus consist of 3 IM doses of from 0.5 to 2.0 ml of vaccine.

The foregoing illustrative examples are particularly directed to description of the manufacture of the specific yeast transformation vector, pHBs-1[GPD], A.T.C.C. No. 40053, and to the use of the vector in yeast transformation resulting in expression of a specific proteinaceous material, HBsAg. The scope of the present invention is clearly not limited, however, to the particular vector manufactured or the particular proteinaceous products produced.

With respect to the specific G-3-PDH promoter/regulator DNA sequence incorporated in pHBs-1[GPD], it is expected that equivalent results in the promotion and regulation of transcription of exogenous DNA will attend the use of DNA fragments of at least somewhat smaller size than the 680 base pair fragment of the examples without significant decreases in levels of expression. In a like manner, it is not unlikely that further reconstruction of pHBs-1[GPD] to restore the approximately 25 base pairs present in the endogenous yeast sequence and/or to delete the approximately 126 base pairs intermediate the exogenous polypeptide coding region and the promoter/regulator sequence will result in enhancement of expression. Such a procedure would involve synthesizing an oligonucleotide as a BamHI to XbaI fragment. The sequences adjacent to the BamHI site would include the untranslated G-3-PDH leader sequence not present in the 680 bp TaqI fragment (i.e., the 26 bp sequence illustrated in Example 3). After the ATG, the first 32 codons of the surface antigen gene would be resynthesized with codons known to be preferentially, optimally or highly frequently utilized in yeast (Grantham, et al., *Nucleic Acids Research*, 8, pp. r49-r62 (1980); Grantham, et al., *Nucleic Acids Research*, 8, pp. 1893-1912 (1980); and, Grantham, et al., *Nucleic Acids Research*, 9, pp. r43-r74 (1981).

Illustrative of such a sequence is the following:

BamHI

5'-GATCCGAATAAACACATAAATAAACAAA
   GCTTATTTGTGTATTTATTTGTTT

-continued

| 1 | | | | 5 | | | | | 10 | | |
|---|---|---|---|---|---|---|---|---|---|---|---|
| Met | Glu | Asn | Ile | Thr | Ser | Gly | Phe | Leu | Gly | | |
| ATG | GAA | AAC | ATT | ACT | TCT | GGT | TTC | TTG | GGT | | |
| TAC | CTT | TTG | TAA | TGA | AGA | CCA | AAG | AAC | CCA | | |
| | | | | 15 | | | | | 20 | | |
| Pro | Leu | Leu | Val | Leu | Gln | Ala | Gly | Phe | Phe | | |
| CCA | TTG | TTG | GTT | TTG | CAA | GCT | GGT | TTC | TTC | | |
| CGT | AAC | AAC | CAA | AAC | GTT | CGA | CCA | AAG | AAG | | |
| | | | | 25 | | | | | 30 | | |
| Leu | Leu | Thr | Arg | Ile | Leu | Thr | Ile | Pro | Gln | Ser | |
| TTG | TTG | ACT | AGA | ATT | TTG | ACT | ATT | CCA | CAA | AGT | |
| AAC | AAC | TGA | TCT | TAA | AAC | TGA | TAA | GGT | GTT | TCA | GAT C-5' |
| | | | | | | | | | | | XbaI |

Alternative sequences which could suitably be employed would provide: the isoleucine-specifying codons as 5'-ATC rather than 5'-ATT;
TAG TAA 5'-ACC rather than 5'-ACT;
TGG TGA the threonine-specifying codons as 5'-TCC rather than 5'-TCT;
AGG AGA the serine-specifying codons as 5'-GTC rather than 5'-GTT;
CAG CAA the valine-specifying codons as 5'-GCC rather than 5'-GCT.
CGG CGA and the alanine-specifying codons as Each of these potential replacements would be consistent with predominant patterns of yeast codon usage for highly expressed endogenous yeast genes. In general, construction of a wholly manufactured sequence comprising all or part of an exogenous gene to be expressed in yeast according to the invention would avoid, to the extent consistent with manufactured sequence manipulations, usage of 5'-CTG for leucine, 5'-TCG for serine, 5'-CCG for proline, and
GAC AGC GGG 5'-CGC or 5'-CGG for arginine.
GCG GCC Such fragments would then be cloned into pHBs-1 and the G-3-PDH promoter/regulator fragment would substantially be cloned into the BamHI site. In a like manner, the remainder of the HBsAg gene could be resynthesized using optimal yeast codons. This would be expected to result in expression levels of HBsAg in yeast comparable to those of G-3-PDH (1–5% of cellular protein). Such a synthetic approach would allow for synthesis in yeast of HBsAg of all serotypes, providing for vaccines protective against all known serotypes of Hepatitis B.

It is clearly the case that numerous DNA sequences coding for exogenous polypeptide may be substituted for the HBsAg polypeptide coding sequence present in pHBsl[GPD] to provide for high level expression of corresponding proteinaceous materials by transformed yeast cells. [Indeed, it is contemplated that active HBsAg preparations may be obtained through use of vectors including DNA sequences coding for relatively short polypeptides possessing the immunological activity of 22 nm particles.] In keeping with the results and proposals of prior investigations, it is expected that highest levels of expression will attend the use of intron-free DNA sequences which incorporate, to the greatest degree possible, alternative codons of the type preferentially expressed in yeast cells.

In the foregoing illustrative examples, a transcription termination and/or poly-A addition sequence was supplied in close proximity to the exogenous gene to be expressed in the form of an entire yeast TRPl gene and this gene also served as a selectable marker for yeast transformation. Clearly transcription termination and/or poly-A addition sequences may be derived from 3' untranslated regions of yeast genes and supplied to vectors of the invention independently of incorporation of an entire structural gene. In a like manner, marker genes other than TRPl can be employed if desired.

While the ARSl origin of replication was successfully employed to donate autonomous replicative capacity to pHBs-l[GPD] in the foregoing illustrative examples, functionally equivalent origin of replication sequences such as a part or all of the 2μ replicon may be employed. For example, two vectors were recently prepared using an approximately 2800 base pair SalI to BglII fragment of pHBs-l[GPD] which included the yeast G-3-PDH promoter/regulator region, the HBsAg gene and the entire yeast TRP-1 gene (along with a small DNA sequence of pBR322 origin) but not the ARS 1 segment. Construction of such vectors is illustrated in FIGS. 3 and 4. In a first construction, this 2800 base pair fragment was inserted into the large fragment obtained by SalI and BamHI digestion of plasmid pGT40 to provide plasmid p(GPD-HBs)-2 including the Ori and Rep 2 sequences (between adjacent EcoRI sites) but not the Rep 1 sequence. In a second construction, the 2800 base pair fragment was inserted into the large fragment obtained by SalI and BamIH digestion of plasmid pGT41 to provide plasmid p(GPD-HBs)-3 including the Ori and both Rep 1 and Rep 2 sequences. Plasmid p(GPD-HBs)-2 is expected to be suitable for use in transformation of $Cir^+$ yeast strains while p(GPD-HBs)-3 can be employed to transform $Cir^O$ strains (having no endogenous 2μ plasmid). Preliminary studies have shown an approximately 20 to 50 fold improvement in levels of expression of HBsAg by yeast cells transformed with p(GPD-HBs)-3 as opposed to pHBs-l[GPD].

Numerous modifications and variations in the invention are expected to occur to those skilled in the art upon consideration of the foregoing description. Consequently, only such limitations as appear in the appended claims should be placed on the invention.

What is claimed is:

1. A yeast cell transformation vector comprising: (1) a DNA transcription promoter/regulator DNA sequence duplicative of that endogenous to yeast cell synthesis of mRNA coding for glyceraldehyde-3-phosphate dehydrogenase wherein said DNA does not include the 26 base pairs having the sequence

CGAATAAACACACATAAATAAACAAA
GCTTATTTGTGTGTATTTATTTGTTT;

(2) a DNA sequence transcribable into mRNA coding for synthesis of a polypeptide exogenous to yeast cells; (3) a DNA sequence duplicative of that coding for termination of transcription or poly-A addition of mRNA in yeast cells; and (4) a DNA sequence operative n yeast cells to confer to said vector the capacity for autonomous DNA replication wherein said yeast is *Saccharomyces cerevisiae.*

2. A yeast cell transformation vector according to claim 1 wherein said DNA sequence transcribable into mRNA coding for synthesis of a polypeptide exogenous to yeast is transcribable into mRNA coding for synthesis of a polypeptide having he immunological activity of HBsAg.

3. A yeast cell transformation vector according to claim 2 wherein the polypeptide coded for has the immunological activity of ADW2 serotype HBsAg.

4. A yeast cell transformation vector according to claim 3 wherein the polypeptide coded for has an amino acid sequence substantially comprising:

```
1               5              10             15
Met Glu Asn Ile Thr Ser Gly Phe Leu Gly Pro Leu Val Leu 20             25             30
Gln Ala Gly Phe Phe Leu Leu Thr Arg Ile Leu Thr Ile Pro Gln 35             40             45
Ser Leu Asp Ser Trp Trp Thr Ser Leu Asn Phe Leu Gly Gly Ser 50             55             60
Pro Val Cys Leu Gly Gln Asn Ser Gln Ser Pro Thr Ser Asn His 65             70             75
Ser Pro Thr Ser Cys Pro Pro Ile Cys Pro Gly Tyr Arg Trp Met 80             85             90
Cys Leu Arg Arg Phe Ile Ile Phe Leu Phe Ile Leu Leu Leu Cys 95             100            105
Leu Ile Phe Leu Leu Val Leu Leu Asp Tyr Gln Gly Met Leu Pro 110            115            120
Val Cys Pro Leu Ile Pro Gly Ser Thr Thr Thr Ser Thr Gly Pro 125            130            135
Cys Lys Thr Cys Thr Thr Pro Ala Gln Gly Asn Ser Met Phe Pro 140            145            150
Ser Cys Cys Cys Thr Lys Pro Thr His Gly Asn Cys Thr Cys Ile 155            160            165
Pro Ile Pro Ser Ser Trp Ala Phe Ala Lys Tyr Leu Trp Glu Trp 170            175            180
Ala Ser Val Arg Phe Ser Trp Leu Ser Leu Leu Val Pro Phe Val 185            190            195
Gln Trp Phe Val Gly Leu Ser Pro Thr Val Trp Leu Ser Ala Ile 200            205            210
Trp Met Met Trp Tyr Trp Gly Pro Ser Leu Tyr Ser Ile Val Ser 215            220            225
Pro Phe Ile Pro Leu Leu Pro Ile Phe Phe Cys Leu Trp Val Tyr

Ile.
```

5. A yeast cell transformation vector according to claim 1 wherein said DNA sequence coding for termination of transcription and/or poly-A addition of mRNA is a sequence substantially duplicative of a sequence functionally associated with a TRP1 gene of yeast origin.

6. A yeast cell transformation vector according to claim 1 wherein said DNA sequence operative to confer autonomous DNA replication is substantially duplicative of a yeast DNA replication origin sequence selected from the group consisting of ARS and 2μ replicon sequences.

7. A yeast cell transformation vector according to claim 1 comprising (1) a DNA transcription promoter/regulator DNA sequence duplicative of that endogenous to yeast cell synthesis of mRNA coding for glyceraldehyde-3-phosphate dehydrogenase wherein said DNA does not include the 26 base pairs having the sequence

CGAATAAACACACATAAATAAACAAA
GCTTATTTGTGTGTATTTATTTGTTT;

(2) a DNA sequence transcribable into mRNA coding for synthesis of a polypeptide exogenous to yeast cells; (3) a DNA sequence duplicative of that coding for termination of transcription and poly-A addition of mRNA in yeast cells; and (4) a DNA sequence operative in yeast cells to confer to said vector the capacity for autonomous DNA replication.

8. A yeast cell transformation vector according to claim 1 wherein said transcription promoter/regulator DNA sequence is substantially duplicative of an approximately 680 base pair DNA sequence derived by TaqI restriction endonuclease enzyme digestion of a 2.1 kilobase Hind III DNA fragment of *Saccharomyces cerevisiae* S288C origin containing a yeast glyceraldehyde-3-phosphate dehydrogenase gene wherein said DNa does not include the 26 base pairs having the sequence

CGAATAAACACACATAAATAAACAAA
GCTTATTTGTGTGTATTTATTTGTTT.

9. Plasmid HBs-1[GPO], A.T.C.C. No. 40053.

10. A yeast cell transformation vector capable of autonomous replication in yeast and useful in securing expression by transformed yeast cells of a polypeptide having the immunological activity of HBsAg, said vector comprising (1) a DNA transcription promoter/regulator DNA sequence duplicative of that endogenous to yeast cell synthesis of mRNA coding for glyceraldehyde-3-phosphate dehydrogenase wherein said DNA does not include the 26 base pairs having the sequence

CGAATAAACACACATAAATAAACAAA
GCTTATTTGTGTGTATTTATTTGTTT;

and (2) an exogenous DNa sequence transcribable into mRNA coding for synthesis of a polypeptide having the immunological activity of HBsAg wherein said yeast is *Saccharomyces cerevisiae.*

* * * * *

UNITED STATES PATENT AND TRADEMARK OFFICE
CERTIFICATE OF CORRECTION

Page 1 of 7

PATENT NO. : 4,977,092

DATED : December 11, 1990

INVENTOR(S) : Bitter

Figure 2:
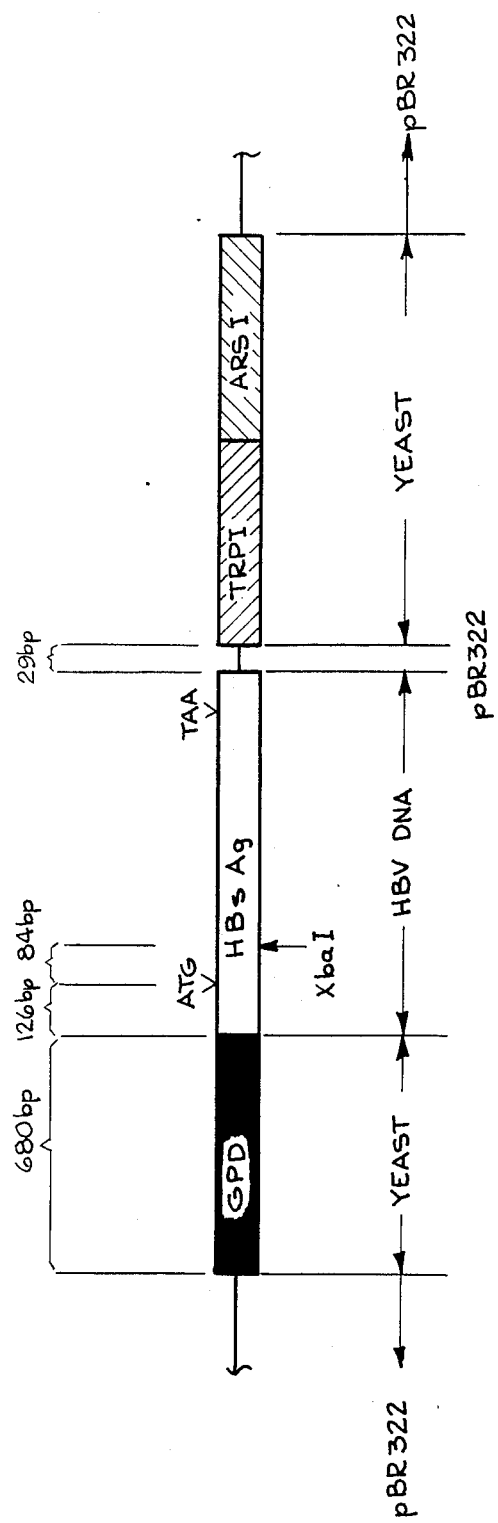
FIG. 2 shows a restriction map of part of pHBs-1[GPD].
Figure 3:
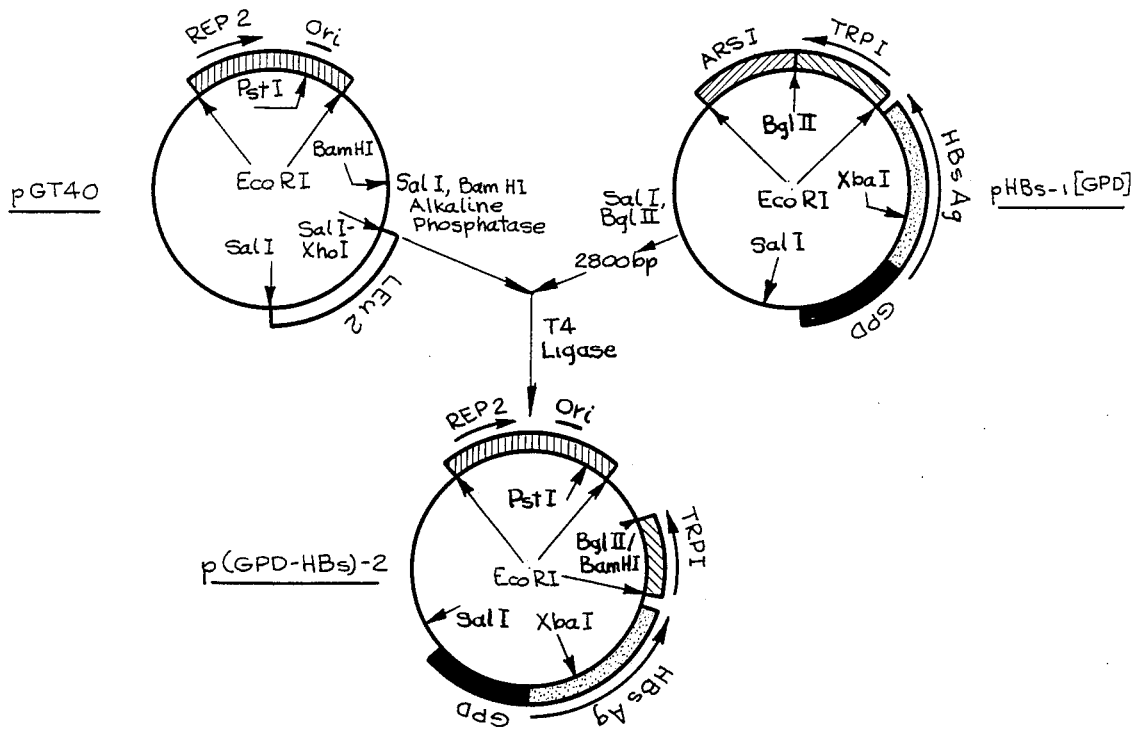
FIG. 3 shows the construction of p(GPD-BGs)-2.
Figure 4:
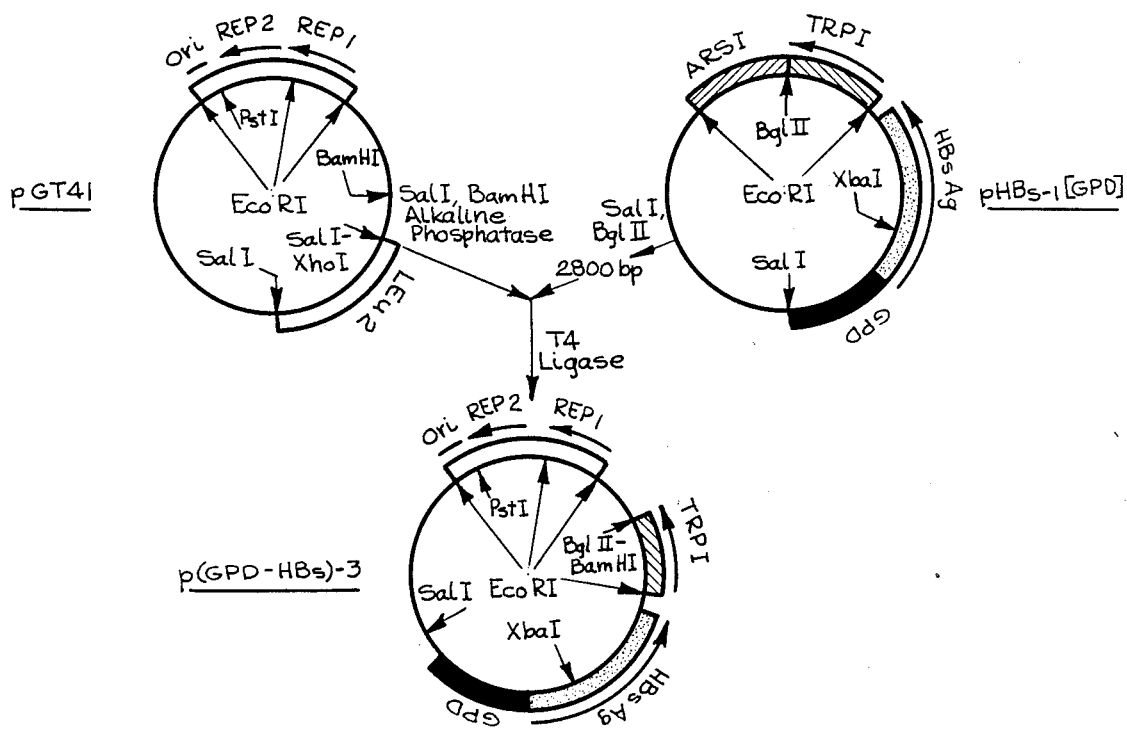
FIG. 4 shows the construction of p(GPD-HBs)-3.

It is certified that error appears in the above-identified patent and that said Letters Patent is hereby corrected as shown below:

Fig. 1, first segment, "pHB$_3$Ag" should be --pHBsAg--.

Fig. 1, second segment, "DNA Pase I T4 DNA Ligase" should be --DNA Pase I Large Fragment T4 DNA Ligase--.

Column 3, line 47, before "Expression" insert --B.--.

Column 4, line 2, "3-phosphoglycero kinase" should be --3-phosphoglycerokinase--.

Column 4, lines 4-5, "dehyrogenase" should be --dehydrogenase--.

UNITED STATES PATENT AND TRADEMARK OFFICE
CERTIFICATE OF CORRECTION

PATENT NO. : 4,977,092

DATED : December 11, 1990

INVENTOR(S) : Bitter

It is certified that error appears in the above-identified patent and that said Letters Patent is hereby corrected as shown below:

Column 6, lines 67-68,

"1          5               10              15
Met Glu Asn Ile Thr Ser Gly Phe Leu Gly Pro Leu Val Leu"

should be

--1         5               10              15
Met Glu Asn Ile Thr Ser Gly Phe Leu Gly Pro Leu Leu Val Leu--.

Column 8, lines 52-53, "glyceraldehydge-3-phosphate" should be --glyceraldehyde-3-phosphate--.

Column 10, line 22, "pHBs-1[GPD[" should be --pHBs-1[GPD]--.

Column 10, line 25, "p(GPD-BGs)-2" should be --p(GPD-HBs)-2--.

Columns 10-11, Table 1 should read as follows:

--TABLE 1

| Amino Acid | "Optimal" Codon |
|---|---|
| Ala | 5'-GCT or 5'-GCC<br>CGA      CGG |
| Arg | 5'-AGA<br>TCT |

UNITED STATES PATENT AND TRADEMARK OFFICE
CERTIFICATE OF CORRECTION

Page 3 of 7

PATENT NO.  : 4,977,092
DATED       : December 11, 1990
INVENTOR(S) : Bitter

It is certified that error appears in the above-identified patent and that said Letters Patent is hereby corrected as shown below:

TABLE 1 (cont.)

| Amino Acid | "Optimal" Codon |
|---|---|
| Asp | 5'-GAC<br>CTG |
| Asn | 5'-AAC<br>TTG |
| Cys | 5'-TGT<br>ACA |
| Gln | 5'-CAA<br>GTT |
| Glu | 5'-GAA<br>CTT |
| Gly | 5'-GGT<br>CCA |
| His | 5'-CAC<br>GTG |
| Ile | 5'-ATT or 5'-ATC<br>TAA         TAG |
| Leu | 5'-TTG<br>AAC |

UNITED STATES PATENT AND TRADEMARK OFFICE
CERTIFICATE OF CORRECTION

PATENT NO. : 4,977,092
DATED : December 11, 1990
INVENTOR(S) : Bitter

It is certified that error appears in the above-identified patent and that said Letters Patent is hereby corrected as shown below:

TABLE 1 (cont.)

| Amino Acid | "Optimal Codon |
|---|---|
| Lys | 5'-AAG<br>TTC |
| Phe | 5'-TTC<br>AAG |
| Pro | 5'-CCA<br>GGT |
| Thr | 5'-ACT or 5'-ACC<br>TGA      TGG |
| Tyr | 5'-TAC<br>ATG |
| Ser | 5'-TCT or 5'-TCC<br>AGA      AGG |
| Val | 5'-GTT or 5'-GTC<br>CAA      CAG-- |

Column 12, line 24, after "et al." delete --.-- (the second period).

UNITED STATES PATENT AND TRADEMARK OFFICE
CERTIFICATE OF CORRECTION

PATENT NO. : 4,977,092

DATED : December 11, 1990

INVENTOR(S) : Bitter

It is certified that error appears in the above-identified patent and that said Letters Patent is hereby corrected as shown below:

Column 16, lines 65-66,

"5'-GATCCGAATAAACACATAAATAAACAAA
       GCTTATTTGTGTATTTATTTGTTT"

should be

--5'-GATCCGAATAAACACACATAAATAAACAAA
       GCTTATTTGTGTGTATTTATTTGTTT--.

Column 17, lines 6-9,

```
"              15                  20
  Pro Leu Leu Val Leu Gln Ala Gly Phe Phe
  CCA TTG TTG GTT TTG CAA GCT GGT TTC TTC
  CGT AAC AAC CAA AAC GTT CGA CCA AAG AAG"
``` should be

```
--             15                  20
  Pro Leu Leu Val Leu Gln Ala Gly Phe Phe
  CCA TTG TTG GTT TTG CAA GCT GGT TTC TTC
  GGT AAC AAC CAA AAC GTT CGA CCA AAG AAG--.
```

Column 17, line 22, after "5'-ATT" insert --the threonine-specifying codons as--.
                                TAA

UNITED STATES PATENT AND TRADEMARK OFFICE
CERTIFICATE OF CORRECTION

PATENT NO. : 4,977,092
DATED : December 11, 1990
INVENTOR(S) : Bitter

It is certified that error appears in the above-identified patent and that said Letters Patent is hereby corrected as shown below:

Column 17, line 26, "threonine-specifying" should be --serine-specifying--.

Column 17, line 30, "serine-specifying" should be --valine-specifying--.

Column 17, line 34, "the valine-specifying" should be --and the alanine-specifying--.

Column 17, line 38, delete "and the alanine-specifying codons as".

Column 19, line 22, "n" should be --in--.

Column 19, line 29, "he" should be --the--.

Column 19, lines 38-39,

"1          5              10             15
 Met Glu Asn Ile Thr Ser Gly Phe Leu Gly Pro Leu Val Leu"

should read

--1          5              10             15
 Met Glu Asn Ile Thr Ser Gly Phe Leu Gly Pro Leu Leu Val Leu--.

UNITED STATES PATENT AND TRADEMARK OFFICE
CERTIFICATE OF CORRECTION

PATENT NO. : 4,977,092

DATED : December 11, 1990

INVENTOR(S) : December 11, 1990

It is certified that error appears in the above-identified patent and that said Letters Patent is hereby corrected as shown below:

Column 20, line 44, "DNa" should be --DNA--.

Column 20, lines 47-48 are typed correctly but should be spaced as follows:

--CGAATAAACACACATAAATAAACAAA
  GCTTATTTGTGTGTATTTATTTGTTT--.

Column 20, line 50, "HBs-1[GPO]" should be --pHBs-1[GPD]--.

Signed and Sealed this

Twenty-ninth Day of December, 1992

Attest:

DOUGLAS B. COMER

Attesting Officer     Acting Commissioner of Patents and Trademarks